United States Patent [19]

Hermeling et al.

[11] Patent Number: 5,078,838
[45] Date of Patent: Jan. 7, 1992

[54] PREPARATION OF BENZALDEHYDE DIALKYL ACETALS AND NOVEL BENZALDEHYDE DIALKYL ACETALS AND BENZYL ESTERS

[75] Inventors: Dieter Hermeling, Neustadt; Albrecht Harreus, Ludwigshafen; Jochen Wild, Deidesheim; Norbert Goetz, Worms, all of Fed. Rep. of Germany

[73] Assignee: BASF Aktiengesellschaft, Ludwigshafen, Fed. Rep. of Germany

[21] Appl. No.: 499,063

[22] Filed: Mar. 26, 1990

[30] Foreign Application Priority Data

Apr. 21, 1989 [DE] Fed. Rep. of Germany ....... 3913166

[51] Int. Cl.$^5$ ................................. C25B 3/02
[52] U.S. Cl. ........................ 204/59 R; 204/78
[58] Field of Search ..................... 204/59 R, 78

[56] References Cited

U.S. PATENT DOCUMENTS

| 3,448,021 | 6/1969 | Koehl, Jr. ............... | 204/72 |
| 4,011,145 | 3/1977 | Haufe et al. ............ | 204/59 R |
| 4,235,683 | 11/1980 | Degner et al. .......... | 204/78 |
| 4,284,825 | 8/1981 | Degner et al. .......... | 204/59 R |
| 4,298,438 | 11/1981 | Degner et al. .......... | 204/78 |
| 4,318,783 | 3/1982 | Buhmann et al. ....... | 204/59 R |
| 4,411,746 | 10/1983 | Degner et al. .......... | 204/59 R |
| 4,588,482 | 5/1986 | Degner .................... | 204/59 R |

FOREIGN PATENT DOCUMENTS

| 12240 | 1/1982 | European Pat. Off. . |
| 29995 | 5/1983 | European Pat. Off. . |
| 72914 | 10/1984 | European Pat. Off. . |
| 0152801 | 1/1985 | European Pat. Off. . |
| 2848397 | 5/1980 | Fed. Rep. of Germany . |
| 2855508 | 7/1980 | Fed. Rep. of Germany . |
| 2935398 | 3/1981 | Fed. Rep. of Germany . |
| 3421976 | 12/1985 | Fed. Rep. of Germany . |

OTHER PUBLICATIONS

J. Chem. Soc. (1954) 2819.
J. Org. Chem. 51 (1986) 4544.
J. Chem. Soc. (1950) 214.
J. Chem. Soc., Perkin II (1975) 1656.

*Primary Examiner*—John Niebling
*Assistant Examiner*—Steven P. Marquis
*Attorney, Agent, or Firm*—John H. Shurtleff

[57] ABSTRACT

A process for the preparation of benzaldehyde dialkyl acetals of the general formula

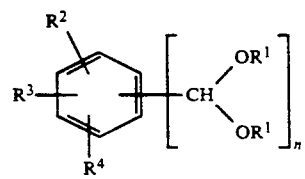

where $R^1$ is alkyl of 1 to 6 carbon atoms, $R^2$, $R^3$ and $R^4$ are hydrogen or halogen, straight-chain, branched or cyclic hydrocarbon radicals or alkoxy, acyloxy, aryloxy or aralkoxy, and n is 1 or 2, in which benzyl derivatives of the general formula

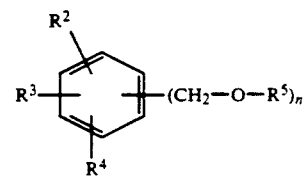

where $R^2$, $R^3$, $R^4$ and n have the abovementioned meanings, $R^5$ is hydrogen or $R^6$—CO—, and $R^6$ is hydrogen or alkyl of 1 to 6 carbon atoms, are anodically oxidized in the presence of an alcohol of the formula $R^1$—OH where $R^1$ has the abovementioned meaning.

8 Claims, No Drawings

PREPARATION OF BENZALDEHYDE DIALKYL ACETALS AND NOVEL BENZALDEHYDE DIALKYL ACETALS AND BENZYL ESTERS

The present invention relates to a process for the preparation of benzaldehyde dialkyl acetals by electrochemical oxidation of benzyl derivatives and to novel halogenated benzaldehyde dialkyl acetals and benzyl esters. Benzaldehyde dialkyl acetals are used, for example, as stable derivatives for storing the relevant benzaldehydes.

The electrochemical oxidation of toluenes to benzaldehyde dialkyl acetals is described, for example, in EP-B 12 240, or DE-A 2 848 397 and 2 935 398. However, good yields of benzaldehyde dialkyl acetals are obtained thereby only if the toluenes contain, in the position para to the methyl group, electron-rich substituents which lower the oxidation potential of the toluenes. Direct electrochemical oxidation of toluenes with electron-poor substituents in the position para to the methyl group, or any substituents in the ortho or meta position, to benzaldehyde dialkyl acetals is either impossible or possible only in poor yields.

U.S. Pat. No. B3,448,021 and J. Org. Chem. 51 (1986) 4544 disclose the electrochemical oxidation of toluenes which are inactivated by a halogen atom to benzyl acetates.

Halogenated benzaldehydes are important intermediates, e.g. for the preparation of active compounds. Thus, for example, 2,4-dihalobenzaldehydes are required for the preparation of N-substituted tetrahydrophthali-mides which are used as herbicides (WO 87/4049). The commonest method for the preparation of such benzalde-hydes is by halogenation of the corresponding toluenes and subsequent hydrolysis of the dihalomethylbenzenes (see Houben-Weyl, "Methoden der organischen Chemie", 4th edition, Volume 5/3, pages 735-738 and Volume 7/1, pages 211-214). Considerable disadvantages in this connection are that dihalomethylbenzenes are potential carcinogens and that large quantities of salt are produced in the hydrolysis. These disadvantages have led to proposals to oxidize toluenes electrochemically. Thus, isomerically pure benzaldehydes can, according to DE 2 855 508, EP 72 914 and EP 29 995, be prepared from the correspondingly substituted toluenes by anodic oxidation. Because it is possible to dispense with the use of environ-mentally undesirable reagents, electrochemical oxidation is superior to other chemical methods. However, the above mentioned difficulties apply to the electrochemical oxidation of toluenes.

Phthalaldehyde acetals can be prepared, for example, by reaction of bis(chloromethyl)benzenes with hexamethylenetetramine (J. Chem. Soc. 1950, 214) and subsequent acetalization with orthoesters (J. Chem. Soc., Perkin II, 1975, 1656) or by anodic oxidation of alkoxymethylbenzenes (DE-A 34 21 976). Alkoxymethylbenzenes are obtained in turn from the corresponding bis(-halomethyl) benzenes (J. Chem. Soc. 1954, 2819). However, the preparation of the intermediates halogenated in the side-chain provides only moderate yields. Since, moreover, large quantities of salt are formed in the hydrolysis and the halogenated intermediates are also potential carcinogens, the environmental acceptability of these syntheses is low.

We have now found that benzaldehyde dialkyl acetals of the general formula I

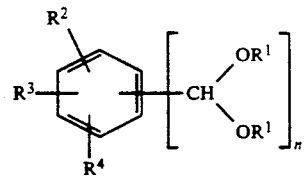

where $R^1$ is alkyl of 1 to 6 carbon atoms, $R^2$, $R^3$ and $R^4$ are hydrogen or halogen, straight-chain, branched or cyclic hydrocarbon radicals or alkoxy, acyloxy, aryloxy or aralkoxy, and n is 1 or 2, are obtained in a particularly advantageous manner when benzyl derivatives of the general formula II

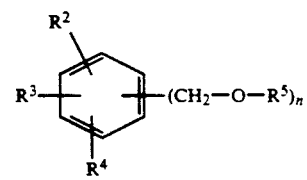

where $R^2$, $R^3$, $R^4$ and n have the abovementioned meanings, $R^5$ is hydrogen or $R^6$—CO— and $R^6$ is hydrogen or alkyl of 1 to 6 carbon atoms, are anodically oxidized in the presence of an alcohol of the formula $R^1$—OH where $R^1$ has the abovementioned meaning.

The particular advantage of the process according to the invention is that isomerically pure benzaldehyde dialkyl acetals are obtained.

Straight-chain, branched or cyclic hydrocarbon radicals suitable as $R^2$, $R^3$ and $R^4$ in the benzyl derivatives of the formula II have, for example, 1 to 18, preferably 1 to 12, carbon atoms. Hydrocarbon radicals of this type are, in particular, straight-chain and branched alkyls, cycloalkyls or aryls. Examples of suitable straight-chain alkyls are methyl, ethyl, propyl, butyl and hexyl. Examples of branched alkyls are those of the formula

which contain a total of at least 3 carbon atoms and in which $R^8$, $R^9$ and $R^{10}$ are alkyls of 1 to 6, preferably 1 to 3, carbon atoms, and $R^{10}$ can also be hydrogen. Examples of suitable radicals of this type are isopropyl, tert-butyl, sec-butyl and iso-butyl. Cyclic hydrocarbon radicals are those which have a cycloalkyl group, a bicycloalkyl group or a benzene or naphthalene ring. The cycloalkyl groups contain, for example, 3 to 8 carbon atoms in the ring, and these in turn can carry alkyls of 1 to 5, preferably 1 to 3, carbon atoms. Examples of cycloalkyl radicals of this type are cyclopropyl, cyclopentyl, cyclohexyl, 3,5-biethylcyclohexyl and tetramethylcyclopropyl. The bicycloalkyl groups contain, for example, 5 to 12 carbon atoms in the rings, and these in turn can contain alkyls of 1 to 5, preferably 1 to 3, carbon atoms. Specific examples of bicycloalkyl groups are: 2-norbornyl, bicyclo[4.1.0]hept-1-yl and 2,6-dimethylbicyclo[4.1.0]hept-1-yl. Examples of aryls are phenyl, 2-chlorophenyl and biphenylyl. Examples of the alkoxy, acyloxy, aryloxy and aralkoxy radicals mentioned as other substituents are methoxy, ethoxy, acetoxy, benzoyloxy, phenoxy, chlorophenoxy and tert-butylphenoxy. Preferred halogens are fluorine, chlorine and bromine.

The benzyl esters of the formula II used as starting materials for the process according to the invention, some of which are novel, can be obtained by electrochemical oxidation of the corresponding toluenes of the formula IV

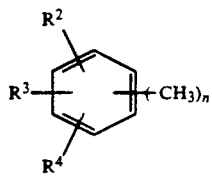

in the presence of an alkanoic acid of the formula $R^6COOH$ where $R^6$ has the abovementioned meaning.

Thus, the benzaldehyde dialkyl acetals of the formula I can be prepared particularly advantageously in two consecutive steps of electrochemical oxidation from the easily obtainable toluenes of the formula IV whose electrochemical alkoxylation in one stage is impossible or possible only in poor yields. The further advantage emerging from this is that the material discharged from the electrolytic acyloxylation can, after removal of solvent and auxiliary electrolyte, be used directly, without further purification, for the anodic alkoxylation.

The two electrochemical oxidations, i.e. the process according to the invention for the preparation of the benzaldehyde dialkyl acetals of the formula I, and the process for the preparation of the benzyl esters of the formula III from the toluenes of the formula IV, can be carried out in conventional electrolysis cells. Undivided continuous-flow cells are preferably used. Examples of anode materials are noble metals such as platinum or oxides such as $RuO_2$, $Cr_2O_3$ or $TiO_x/RuO_x$. Graphite anodes are preferably used. Suitable cathode materials include iron, steel, nickel, noble metals such as platinum, or graphite.

The electrolytes used for the anodic alkoxylation contain the benzyl derivative of the formula II, the alcohol of the formula $R^1OH$ and, to increase the conductivity, an auxiliary electrolyte. Auxiliary electrolytes which can be used are the conducting salts conventional in electrochemistry, such as fluorides, e.g. KF, tetrafluoroborates, e.g. sodium tetrafluoroborate, alcoholates, e.g. sodium methylate, sulfonates, e.g. sodium benzenesulfonate or alkyl sulfates, e.g. sodium methyl sulfate.

Examples of the composition of the electrolyte are as follows:

1 to 49, preferably 5 to 30, % by weight of benzyl compound of the formula II,
50 to 99, preferably 70 to 95, % by weight of alcohol of the formula $R^1OH$ and
0.1 to 5, preferably 0.25 to 2, % by weight of auxiliary electrolyte.

Electrolysis is expediently carried out at current densities from 0.2 to 25 $A/dm^2$ and at up to about 100° C., expediently from 0° C. to about 5° C. below the boiling point of the alcohol. Extensive reaction of the benzyl esters and benzyl alcohols is possible. The material discharged from the electrolysis is worked up by conventional methods, preferably by distillation. Excess alcohol, conducting salt and any unreacted benzyl derivative of the formula II can be returned to the electrolysis.

The electrolyte used for the acyloxylation is a solution of the toluene derivative of the formula IV in an alkanoic acid of the formula $R^6COOH$, to which an auxiliary electrolyte is added to increase the conductivity. It is also possible to add a cosolvent to increase the solubility of the toluenes. Examples of suitable cosolvents are ketones such as acetone or methyl ethyl ketone, nitriles such as acetonitrile or propionitrile, and anhydrides such as acetic anhydride. The abovementioned conducting salts, for example, are used as auxiliary electrolytes. Examples of compositions of electrolytes suitable for the electrochemical acyloxylation are as follows:

1 to 40% by weight of toluene of the general formula IV, 1 to 10% by weight of conducting salt, 0 to 20% by weight of cosolvent and 5 to 95% by weight of alkanoic acid.

The current densities and electrolysis temperatures can be varied within wide limits. Thus, for example, electrolysis is carried out at from 0.2 to 25 $A/dm^2$ and at from 15° to 95° C. Extensive reaction of the toluenes is possible, and the material discharged from the electrolysis is worked up by conventional methods, e.g. by distillation, extraction and crystallization. Cosolvent, excess alkanoic acid and conducting salt can, after removal from the benzyl esters, be returned together with any unreacted toluene to the electrolysis.

Examples of suitable alcohols of the formula $R^1OH$ are methanol, ethanol, propanol and butanol. Examples of carboxylic acids of the formula $R^6COOH$ are formic acid, acetic acid and propionic acid.

The present invention also relates to the novel halogenated benzaldehyde dialkyl acetals and benzyl esters of the general formulae

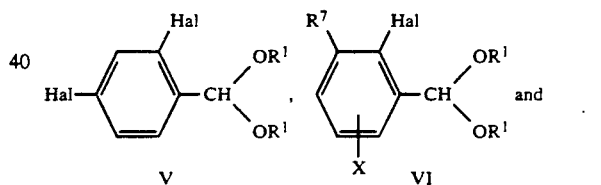

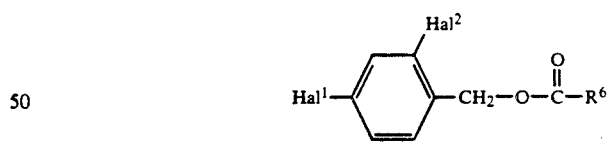

where Hal is halogen, $R^1$ is alkyl of 1 to 6, preferably 1 to 4, carbon atoms, $R^7$ is a straight-chain, branched or cyclic hydrocarbon radical of 1 to 18 carbon atoms, X is hydrogen or halogen, $Hal^1$ is halogen, $Hal^2$ is halogen different from $Hal^1$, and $R^6$ is hydrogen or alkyl of 1 to 6, preferably 1 to 4, carbon atoms. The novel benzaldehyde dialkyl acetals of the formula VI which are of particular industrial interest are those in which $R^7$ is a branched or cyclic alkyl of 3 to 12, in particular 3 to 8, carbon atoms.

The novel benzaldehyde dialkyl acetals of the formulae V and VI can easily be hydrolyzed to the corresponding benzaldehydes. They are therefore stable derivatives for storing benzaldehydes of the formulae

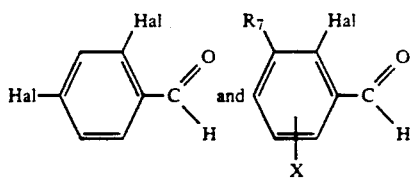

VIII                IX

The diacetals are hydrolyzed by conventional methods, for example by simply heating in water with the addition of catalytic amounts of acid at from 40° to 95° C.

Examples of 2,4-dihalotoluenes which are used for the preparation of benzyl esters of the formula III and of the benzaldehyde dialkyl acetals of the formula V are 2,4-dichlorotoluene, 2,4-difluorotoluene, 2-chloro-4-fluorotoluene, 2,4-dibromotoluene, 2-fluoro-4-chlorotoluene and 2-bromo-4-fluorotoluene.

Examples of suitable benzyl derivatives of the formula II which are used for the preparation of the novel benzaldehyde dialkyl acetals of the formula VI are the compounds of the formula

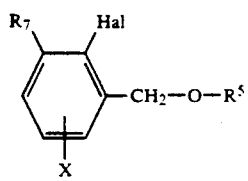

which are shown in the table which follows.

| No. | Hal | $R^7$ | $R^5$ | X |
|---|---|---|---|---|
| 1 | Cl | cyclopropyl | $CH_3-CO-$ | H |
| 2 | Cl | $-CH(CH_3)-CH_2-CH_3$ | $CH_3-CO-$ | H |
| 3 | Br | $-CH(CH_3)_2$ | H | H |
| 4 | Br | $-CH(CH_3)_2$ | $CH_3-CO-$ | H |
| 5 | Cl | cyclohexyl | $CH_3-CO-$ | H |
| 6 | Cl | cyclohexyl | H | H |
| 7 | F | $-CH(CH_3)_2$ | H | H |
| 8 | F | $-CH(CH_3)_2$ | $CH_3-CO-$ | H |
| 9 | Cl | cyclopentyl | H | H |
| 10 | Cl | cyclopentyl | $CH_3-CO-$ | H |
| 11 | F | cyclopentyl | H | 6-Cl |
| 12 | F | cyclopentyl | $CH_3-CO-$ | 6-Cl |
| 13 | Cl | $-CH(CH_3)_2$ | $CH_3-CO-$ | H |
| 14 | Cl | $-CH(CH_3)_2$ | H | H |
| 15 | Cl | $-CH(CH_3)_2$ | $CH_3-CO-$ | 6-F |
| 16 | Cl | $-CH(CH_3)_2$ | H | 6-F |
| 17 | Cl | $-C(CH_3)_3$ | $CH_3CO-$ | H |
| 18 | Cl | $-C(CH_3)_3$ | H | H |
| 19 | Cl | $-CH(CH_3)-CH_2-CH_3$ | H | H |
| 20 | F | cyclopentyl | $CH_3-CO-$ | H |
| 21 | F | cyclopentyl | H | H |
| 22 | Cl | $-CH(CH_3)_2$ | $H-CO-$ | H |
| 23 | Cl | $-CH(CH_3)_2$ | $CH_3-CH_2-CO-$ | H |
| 24 | F | $-C(CH_3)_3$ | $CH_3-CO-$ | H |
| 25 | F | $-C(CH_3)_3$ | H | H |

EXAMPLE 1

2-Methylbenzaldehyde dimethyl acetal a) Electrochemical synthesis of 2-methylbenzyl acetate o-Xylene is electrolyzed under the stated conditions in the electrolysis cell which is described below.

Apparatus: undivided cell with 11 bipolar electrodes
Anode: graphite
Electrolyte: 1350 g (12.74 mol) of o-xylene, 270 g of acetic anhydride, 270 g of triethylmethylammonium methyl sulfate and 7110 g of acetic acid
Cathode: graphite
Current density: 1.33 A/dm²
Electrolysis temperature: 75° C.

Electrolysis with 2.75 F/mol of o-xylene. The electrolyte is pumped at 200/h through the cell during the electrolysis. After the electrolysis is complete, acetic acid/anhydride are removed by distillation under atmospheric pressure up to 150° C., and the residue is partitioned between water and methyl tert-butyl ether. Methyl tert-butyl ether is removed from the organic phase by distillation under atmospheric pressure. 1930 g of residue are obtained and contain, according to analysis by gas chromatography, 79.4 g (5%) of 2-methylbenzaldehyde and 22 g (59%) of 2-methylbenzyl acetate. Pure 2-methylbenzyl acetate is obtained by distillation at 72° C. under 2 mbar.

b) Electrochemical synthesis of 2-methylbenzaldehyde dimethyl acetal 2-Methylbenzyl acetate is oxidized in the electrolysis cell described in paragraph (a) under the following conditions:

Electrolyte: 375 g (2.287 mol) of 2-methylbenzyl acetate, 18.75 g of sodium benzenesulfonate, 6.25 g of sodium methylate and 2100 g of methanol Current density: 3.4 A/dm$^2$
Electrolysis temperature: 25° C.
Electrolysis with 3.75 F/mol of 2-methylbenzyl acetate. The electrolyte is pumped at 200/h through the cell during the electrolysis. After the electrolysis is complete, the methanol is removed by distillation under atmospheric pressure, the precipitated conducting salt is removed by filtration, and the filtrate is purified by distillation under reduced pressure. 14.6 g (5%) of 2-methylbenzaldehyde and 248.5 g (66%) of 2-methylbenzaldehyde dimethyl acetal (boiling point: 46°–48° C./2 mbar) are obtained.

EXAMPLE 2

3-Methylbenzaldehyde dimethyl acetal a) Electrochemical synthesis of 3-methylbenzyl acetate m-Xylene is electrolyzed in the electrolysis cell described in Example 1a under the following conditions:
Electrolyte: 900 g (8.49 mol) of m-xylene, 180 g of triethylmethylammonium methyl sulfate, 180 g of acetic anhydride and 4740 g of acetic acid
Current density: 1 A/dm$^2$
Electrolysis temperature: 77° C.
Electrolysis with 3.25 F/mol of m-xylene. The electrolyte is pumped at 200/h through the cell during the electrolysis. Working up is carried out as described in Example 1a). Distillation under reduced pressure to purify results in 566.4 g (41%) of 3-methylbenzyl acetate (boiling point 75° C./2 mbar).

b) Electrochemical synthesis of 3-methylbenzaldehyde dimethyl acetal 3-Methylbenzyl acetate is oxidized in the electrolysis cell described in Example 1a under the following conditions:
Electrolyte: 375 g (2.29 mol) of 3-methylbenzyl acetate, 18.75 g of sodium benzenesulfonate, 6.25 g of sodium methylate and 2100 g of methanol
Current density: 3.4 A/dm$^2$
Electrolysis temperature: 25° C.
Electrolysis with 3.5 F/mol of 3-methylbenzyl acetate. The electrolyte is pumped at 200/h through the cell during the electrolysis. The material discharged from the electrolysis is worked up as described in Example 1b). Distillation under reduced pressure to purify results in 14.9 g (5%) of 3-methylbenzaldehyde and 229.3 g (60%) of 3-methylbenzaldehyde dimethyl acetal (boiling point 62° C./3 mbar).

EXAMPLE 3

3,5-Dimethylbenzal dimethyl acetal a) Electrochemical synthesis of 3,5-dimethylbenzyl acetate Mesitylene is electrolyzed in the electrolysis cell described in Example 1a under the following conditions:
Electrolyte: 945 g (7.875 mol) of mesitylene, 210 g of potassium benzenesulfonate, 945 g of acetic anhydride and 5300 g of acetic acid
Current density: 0.5 A/dm$^2$
Electrolysis temperature: 70° C.
Electrolysis with 2.5 F/mol of mesitylene. The electrolyte is pumped at 200/h through the cell during the electrolysis. The material discharged from the electrolysis is worked up as described in Example 1a). Distillation under reduced pressure to purify results in 698.1 g (50%) of 3,5-dimethylbenzyl acetate (boiling point 96° C./1 mbar).

b) Electrochemical synthesis of 3,5-dimethylbenzaldehyde dimethyl acetal 3,5-Dimethylbenzyl acetate is oxidized in the electrolysis cell described in Example 1a under the following conditions:
Electrolyte: 665 g (3.736 mol) of 3,5-dimethylbenzyl acetate, 30 g of sodium benzenesulfonate, 30 g of sodium methylate and 5290 g of methanol
Current density: 3.4 A/dm$^2$
Electrolysis temperature: 40° C.
Electrolysis with 5 F/mol of 3,5-dimethylbenzyl acetate. The electrolyte is pumped at 200/h through the cell during the electrolysis. The material discharged from the electrolysis is worked up as described in Example 1b). With a degree of oxidation of 89%, distillation under reduced pressure to purify results in 18.1 g (4%) of 3,5-dimethylbenzaldehyde and 292.4 g (44%) of 3,5-dimethylbenzaldehyde dimethyl acetal (boiling point 67° C./2 mbar). The selectivity calculated from this is 54%.

EXAMPLE 4

4-Fluorobenzaldehyde dimethyl acetal a) Electrochemical synthesis of 4-fluorobenzyl acetate 4-Fluorotoluene is electrolyzed in the electrolysis cell described in Example 1a under the following conditions:
Electrolyte: 190 g (1.727 mol) of 4-fluorotoluene, 190 g of acetic anhydride, 57 g of triethylmethylammonium methyl sulfate and 1663 g of acetic acid
Current density: 1.33 A/dm$^2$
Electrolysis temperature: 70° C.
Electrolysis with 3.75 F/mol of 4-fluorotoluene. The electrolyte is pumped at 200/h through the cell during the electrolysis. The material discharged from the electrolysis is worked up as described in Example 1a). 232 g of residue are obtained and contain, according to analysis by gas chromatography, 43 g (22%) of 4-fluorotoluene, 11.3 g (5%) of 4-fluorobenzaldehyde and 179.3 g (62%) of 4-fluorobenzyl acetate. Pure 4-fluorobenzyl acetate is obtained by distillation at 70° C. under 2 mbar.

b) Electrochemical synthesis of 4-fluorobenzaldehyde dimethyl acetal 4-Fluorobenzyl acetate is oxidized in the electrolysis cell described in Example 1a under the following conditions:
Electrolyte: 250 g (1.488 mol) of 4-fluorobenzyl acetate, 12.5 g of sodium benzenesulfonate, 12.5 g of sodium methylate and 2225 g of methanol
Current density: 3.4 A/dm$^2$
Electrolysis temperature: 25° C.
Electrolysis with 4 F/mol of 4-fluorobenzyl acetate. The electrolyte is pumped at 200/h through the cell during the electrolysis. After the electrolysis is complete, the discharged material is adjusted to pH 8 to 10 with sodium methylate and then worked up as described in Example 1b). With a degree of oxidation of 94%, distillation under reduced pressure to purify results in 7.7 g (4%) of 4-fluorobenzaldehyde and 135.4 g (54%) of 4-fluorobenzaldehyde dimethyl acetal (boiling point 42° C./2 mbar). The selectivity calculated from this is 62%.

EXAMPLE 5

2-Fluorobenzaldehyde dimethyl acetal a) Electrochemical synthesis of 2-fluorobenzyl acetate 2-Fluorotoluene is oxidized in the electrolysis cell described in Example 1a under the following conditions:

Electrolyte: 1013 g (9.206 mol) of 2-fluorotoluene, 675 g of acetic anhydride, 338 g of triethylmethylammonium methyl sulfate and 4727 g of acetic acid Current density: 1.33 A/dm$^2$
Electrolysis temperature: 75° C.

Electrolysis with 4.5 F/mol of 2-fluorotoluene. The electrolyte is pumped at 200/h through the cell during the electrolysis. The material discharged from the electrolysis is worked up as described in Example 1a). Distillation under reduced pressure to purify results in 835.2 g (54%) of 2-fluorobenzyl acetate (boiling point 80° C./4 mbar).

b) Electrochemical synthesis of 2-fluorobenzaldehyde dimethyl acetal 2-Fluorobenzyl acetate is oxidized in the electrolysis cell described in Example 1a under the following conditions:

Electrolyte: 740 g (4.405 mol) of 2-fluorobenzyl acetate, 50 g of sodium benzenesulfonate, 25 g of sodium methylate and 4185 g of methanol.

Current density: 3.4 A/dm$^2$
Electrolysis temperature: 40° C.

Electrolysis with 7 F/mol of 2-fluorobenzyl acetate. The electrolyte is pumped at 200/h through the cell during the electrolysis. After the electrolysis is complete, the material discharged is adjusted to pH 8-10 with sodium methylate and then worked up as described in Example 1b). With a degree of oxidation of 91%, distillation under reduced pressure to purify results in 348.8 g (47%) of 2-fluorobenzaldehyde dimethyl acetal (boiling point 40° C./2 mbar). The selectivity of the anodic methoxylation is accordingly 52%.

EXAMPLE 6

4-(4-Methylphenyl)benzaldehyde dimethyl acetal a) Electrochemical synthesis of 4-(4-methylphenyl) benzyl acetate 4-(4-Methylphenyl)toluene is oxidized in the electrolysis cell described in Example 1a under the following conditions:

Electrolyte: 350 g (1.923 mol) of 4-(4-methylphenyl)-toluene, 600 g of acetic anhydride, 186 g of potassium benzenesulfonate and 6200 g of acetic acid Current density: 0.33 A/dm$^2$
Electrolysis temperature: 70° C.

Electrolysis with 3 F/mol of 4-(4-methylphenyl)-toluene. The electrolyte is pumped at 200/h through the cell during the electrolysis. The material discharged from the electrolysis is worked up as described in Example 1a). Distillation under reduced pressure to purify results in 5.5 g (2%) of 4-(4-methylphenyl)toluene and 245.1 g (53%) of 4-(4-methylphenyl)benzyl acetate (boiling point 172°-178° C./3 mbar; melting point 46° C.).

b) Electrochemical synthesis of 4-(4-methylphenyl) benzaldehyde dimethyl acetal 4-(4-Methylphenyl)benzyl acetate is oxidized in the electrolysis cell described in Example 1a under the following conditions:

Electrolyte: 171 g (0.713 mol) of 4-(4-methylphenyl)-benzyl acetate, 30 g of sodium benzenesulfonate, 15 g of sodium methylate and 2784 g of methanol Current density: 3.4 A/dm$^2$
Electrolysis temperature: 40° C.

Electrolysis with 6 F/mol of 4-(4-methylphenyl)-benzyl acetate. The electrolyte is pumped at 200/h through the cell during the electrolysis. The material discharged from the electrolysis is worked up as described in Example 1b). With a degree of oxidation of 96.5%, distillation under reduced pressure to purify results in 5.5 g (4%) of 4-(4-methylphenyl)benzaldehyde and 63.3 g (37%) of 4-(4-methylphenyl)benzaldehyde dimethyl acetal (boiling point 148°-15° C./3 mbar). The selectivity calculated from this is 42.5%.

EXAMPLE 7

2-Chloro-4-fluorobenzaldehyde dimethyl acetal a) Electrochemical synthesis of 2-chloro-4-fluorobenzyl acetate 2-Chloro-4-fluorotoluene is oxidized in the electrolysis cell described in Example 1a under the following conditions:

Electrolyte: 1200 g (8.307 mol) of 2-chloro-4-fluorotoluene, 400 g of acetic anhydride, 200 g of triethylmethylammonium methyl sulfate and 6200 g of acetic acid Current density: 1.33 A/dm$^2$
Electrolysis temperature: 70° C.

Electrolysis with 4.5 F/mol of 2-chloro-4-fluorotoluene. The electrolyte is pumped at 200/h through the cell during the electrolysis. The material discharged from the electrolysis is worked up as described in Example 1a. 1575 g of residue are obtained and contain, according to analysis by gas chromatography, 10.1 g of 2-chloro-4-fluorotoluene, 0.1 g of 2-chloro-4-fluorobenzaldehyde and 1081.2 g of 2-chloro-4-fluorobenzyl acetate. Calculated from this are a conversion of 99.2%, a yield of 64.3% and a selectivity of 71.0%. Pure 2-chloro-4-fluorobenzyl acetate is obtained by distillation at 86°-88° C. under 2 mbar.

$^1$H-NMR (300 MHz, CDCl$_3$):

(ppm)=2.12 (s, 3H, CH$_3$COO—); 5.18 (s, 2H, —CH$_2$OAC); 7.0, 7.16, 7.4 (each m, 3H, arom. H)

b) Preparation of 2-chloro-4-fluorobenzaldehyde dimethyl acetal 2-Chloro-4-fluorobenzyl acetate is oxidized in the electrolysis cell described in Example 1a under the following conditions:

Electrolyte: 900 g (4.445 mol) of 2-chloro-4-fluorobenzyl acetate, 30 g of sodium methylate, 90 g of sodium benzenesulfonate and 5040 g of methanol Current density: 3.3 A/dm$^2$
Electrolysis temperature: 45°-50° C.

Electrolysis with 5 F/mol of 2-chloro-4-fluorobenzyl acetate. The electrolyte is pumped at 200/h through the cell during the electrolysis. After the electrolysis is complete, the material discharged is adjusted to pH 7-8 with sodium methylate and worked up as described in Example 1b). Distillation under reduced pressure to purify results in 44.9 g of 2-chloro-4-fluorobenzaldehyde and 675.7 g of 2-chloro-4-fluorobenzaldehyde dimethyl acetal (boiling point 60°-62° C./2 mbar). From this are calculated a yield of 74.2% and a selectivity of 80.6%.

$^1$H-NMR (300 MHz, CDCl$_3$):

(ppm)=3.37 (s, 6H, OCH$_3$); 5.59 (s, 1H —CH-(OCH$_3$)$_2$); 7.0, 7.13, 7.6 (each m, 3H, arom. H).

EXAMPLE 8

Terephthalaldehyde tetramethyl acetal a) Electrochemical synthesis of p-xylylene diacetate p-Xylene is electrolyzed in the electrolysis cell described in Example 1a under the following conditions:

Electrolyte: 300 g (2.83 mol) of p-xylene, 300 g of acetic anhydride, 120 g of triethylmethylammonium methyl sulfate and 2280 g of acetic acid Current density: 1.33 A/dm$^2$
Electrolysis temperature: 75° C.

Electrolysis with 5 F/mol of p-xylene. The electrolyte is pumped at 200/h through the cell during the electrolysis. The material discharged from the electrolysis is worked up as described in Example 1a). Distillation under reduced pressure to purify results in 194.1 g (31%) of p-xylene diacetate (boiling point 125° C./2 mbar).

b) Electrochemical synthesis of terephthalaldehyde tetramethyl acetal p-Xylylene diacetate is oxidized in the electrolysis cell described in Example 1a under the following conditions:

Electrolyte: 450 g (2.027 mol) of p-xylylene diacetate, 15 g of sodium methylate and 2542 g of methanol Current density; 3.4 A/dm$^2$ Electrolysis temperature: 40° C.

Electrolysis with 6.5 F/mol of p-xylylene diacetate with the addition of 30 g of sulfuric acid after 0.5 F/mol. The electrolyte is pumped at 200/h through the cell during the electrolysis. After the electrolysis is complete, the material discharged is adjusted to pH 8 to 9 by addition of sodium methylate and then worked up as described in Example 1b. Distillation under reduced pressure to purify results in 44.8 g (12.3%) of terephthalaldehyde dimethyl acetal and 275.1 g (60.1%) of terephthalaldehyde tetramethyl acetal. The selectivity calculated from this is 72.3%. Pure terephthalaldehyde tetramethyl acetal is obtained by distillation at 115° C. under 5 mbar.

EXAMPLE 9

Isophthalaldehyde tetramethyl acetal a) Electrochemical synthesis of m-xylylene diacetate m-Xylylene is electrolyzed in the electrolysis cell described in Example 1a under the following conditions:

Electrolyte: 450 g (4.245 mol) of m-xylene, 300 g of acetic anhydride, 150 g of triethylmethylammonium methyl sulfate and 2100 g of acetic acid Current density: 1.33 A/dm$^2$ Electrolysis temperature: 75° C.

Electrolysis with 7 F/mol of m-xylene. The electrolyte is pumped at 200/h through the cell during the electrolysis. The material discharged from the electrolysis is worked up as described in Example 1a. Distillation under reduced pressure to purify results in 225.1 g (24%) of m-xylylene diacetate (boiling point 120°-125° C./2 mbar).

b) Electrochemical synthesis of isophthalaldehyde tetramethyl acetal m-Xylylene diacetate is electrolyzed in the electrolysis cell described in Example 1a under the following conditions:

Electrolyte: 216 g (0.973 mol) of m-xylylene diacetate, 30 g of sodium methylate, 15 g of sodium benzenesulfonate and 2755 g of methanol Current density: 3.4 A/dm$^2$ Electrolysis temperature: 40° C.

Electrolysis with 10 F/mol of m-xylylene diacetate. The electrolyte is pumped at 200/h through the cell during the electrolysis. The material discharged from the electrolysis is worked up as described in Example 1b). With a conversion of 89.3%, distillation under reduced pressure to purify results in 59.2 g (27.0%) of isophthalaldehyde tetramethyl acetal. The selectivity calculated from this is 30.2%. Pure isophthalaldehyde tetramethyl acetal is obtained by distillation at 108° C. under 3 mbar.

EXAMPLE 10

2-Chloro-3-isopropylbenzaldehyde dimethyl acetal

2-Chloro-3-isopropylbenzyl acetate is oxidized in the electrolysis cell described in Example 1a under the following conditions:

Electrolyte: 290 g (1.28 mol) of 2-chloro-3-isopropylbenzyl acetate, 30 g of sodium benzenesulfonate, 15 g of sodium methylate and 2665 g of methanol Current. density: 3.3 A/dm$^2$ Electrolysis temperature: 40° C.

Electrolysis with 8 F/mol of 2-chloro-3-isopropylbenzyl acetate. The electrolyte is pumped at 200/h through the cell during the electrolysis. The material discharged from the electrolysis is worked up as described in Example 1b). Distillation under reduced pressure to purify results in 166.7 g (57%) of 2-chloro-3-isopropylbenzaldehyde dimethyl acetal (boiling point 92° C./2 mbar).

$^1$H-NMR (200 MHz, CDCl$_3$): δ (ppm)=1.28 (d, 6H, —CH$_3$), 3.45 (s, 6H, —OCH$_3$); 3.50 (m, 1H, —CH(CH$_3$)$_2$); 5.71 (s, 1H, —CH(OCH$_3$)$_2$); 7.33 (m, 2H, arom. H); 7.51 (m, 1H, arom. H).

EXAMPLE 11

2-Chloro-3-cyclopentylbenzaldehyde dimethyl acetal

2-Chloro-3-cyclopentylbenzyl acetate is oxidized in the electrolysis cell described in Example 1a under the following conditions:

Electrolyte: 98 g (0.388 mol) of 2-chloro-3-cyclopentylbenzyl acetate, 30 g of sodium benzenesulfonate, 15 g of sodium methylate and 2857 g of methanol.

Electrolysis with 18 F/mol of 2-chloro-3-cyclopentylbenzyl acetate. The electrolyte is pumped at 200 1/h through the cell during the electrolysis. The material discharged from the electrolysis is worked up as described in Example 1b). Distillation under reduced pressure to purify results in 40.4 g (41%) of 2-chloro-3-cyclopentylbenzaldehyde dimethyl acetal (boiling point 140°-145° C./4 mbar).

$^1$H-NMR (270 MHz, CDCl$_3$): δ (ppm)=1.5-2.15 (m, 8H, —CH$_2$), 3.34 (s,6H, —OCH$_3$); 3.52 (m, 1H, —CH); 5.63 (s, 1H, —CH(OCH$_3$)$_2$); 7.2 (m, 2H, arom. H); 7.44 (d, 1H, arom. H).

$^{13}$C-NMR (270 MHz, CDCl$_3$): δ (ppm)=25.6 (t, 2C), 33.4 (t, 2C), 42.4 (d), 53.8 (q, 2C), 101.9 (d), 125.7 (d), 126.3 (d), 127.2 (d), 133.3 (s), 136.1 (s), 144.2 (s).

We claim:

1. A process for the preparation of a benzaldehyde dialkyl acetal of the formula I

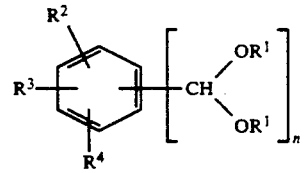

where R$^1$ is alkyl of 1 to 6 carbon atoms, R$^2$, R$^3$ and R$^4$ are hydrogen or halogen, straight-chain, branched or cyclic hydrocarbon radicals or alkoxy, acyloxy, aryloxy or aralkoxy, and n is 1 or 2, which comprises carrying out an electrochemical anodic oxidation of a benzyl derivatives of the formula II

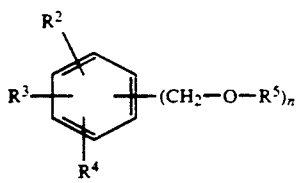

where $R^2$, $R^3$, $R^4$ and n have the abovementioned meanings, $R^5$ is hydrogen or $R^6$—CO—, and $R^6$ is hydrogen or alkyl of 1 to 6 carbon atoms, in the presence of an alcohol of the formula $R^1$—OH where $R^1$ has the abovementioned meaning.

2. A process as claimed in claim 1, wherein an electrolyte with the composition 1 to 49% by weight of benzyl derivative of the formula II, 50 to 99% by weight of an alcohol of the formula $R^1$OH and 0.1 to 5% by weight of an auxiliary electrolyte is used for the electrochemical oxidation.

3. A process as claimed in claim 1, wherein the electrochemical oxidation is carried out at current densities of from 0.2 to 25 A/dm$^2$ and at up to 100° C.

4. A process as claimed in claim 1, wherein the alcohol reactant $R^1$OH is selected from the group consisting of methanol, ethanol, propanol and butanol.

5. A process as claimed in claim 1, wherein the alcohol reactant $R^1$OH is methanol.

6. A process for the preparation of a benzaldehyde dialkyl acetal of the formula

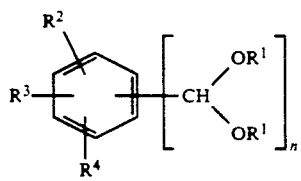

where $R^1$ is alkyl of 1 to 6 carbon atoms, $R^2$, $R^3$ and $R^4$ are hydrogen or halogen, straight-chain, branched or cyclic hydrocarbon radicals or alkoxy, acyloxy, aryloxy or aralkoxy, and n is 1 or 2, which comprises carrying out an electrochemical anodic oxidation of a benzyl ester of the formula

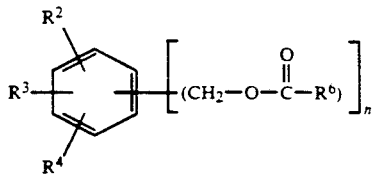

where $R^2$, $R^3$, $R^4$ and n have the abovementioned meanings and $R^6$ is hydrogen or alkyl of 1 to 6 carbon atoms, in the presence of an alcohol of the formula $R^1$—OH where $R^1$ has the abovementioned meaning.

7. A process as claimed in claim 6, in which the benzyl derivative of the formula II which is used is a benzyl ester of the formula III

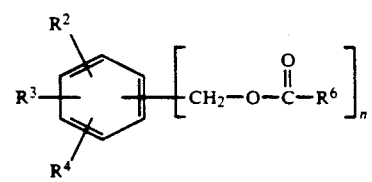

where $R^2$, $R^3$, $R^4$, $R^5$ and n have the meanings specified in claim 6, which has been obtained by electrochemical oxidation of a toluene derivative of the formula IV

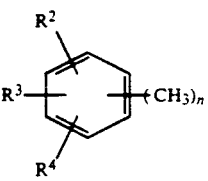

where $R^2$, $R^3$, $R^4$ and n have the abovementioned meanings, in the presence of an alkanoic acid of the formula $R^6$COOH where $R^6$ has the abovementioned meaning.

8. A process as claimed in claim 6, wherein $R^6$ is selected from the group consisting of hydrogen, methyl and ethyl.

* * * * *

UNITED STATES PATENT AND TRADEMARK OFFICE
CERTIFICATE OF CORRECTION

PATENT NO. : 5,078,838

DATED : January 7, 1992

INVENTOR(S) : Hermeling et al

It is certified that error appears in the above-identified patent and that said Letters Patent is hereby corrected as shown below:

Column 12, line 68, Claim 1, line 8, (disregarding the structural formula): change "derivatives" to --derivate--.

Column 14, line 28, Claim 7, line 4, (disregarding the structural formula): change "$R^5$" to --$R^6$--.

Signed and Sealed this

Thirteenth Day of April, 1993

Attest:

STEPHEN G. KUNIN

Attesting Officer      Acting Commissioner of Patents and Trademarks